(12) United States Patent
Tan et al.

(10) Patent No.: US 10,597,413 B2
(45) Date of Patent: Mar. 24, 2020

(54) SILICONE-COMPATIBLE COMPOUNDS

(71) Applicants: HENKEL IP & HOLDING GMBH, Duesseldorf (DE); HENKEL AG & CO. KGAA, Duesseldorf (DE)

(72) Inventors: Wenjuan Tan, Shanghai (CN); Zhixiang Lu, East Lyme, CT (US); Hao Wu, Shanghai (CN); Yong Zhang, Shanghai (CN); Zheng Lu, South Glastonbury, CT (US); Xuelong Hou, Shanghai (CN)

(73) Assignees: HENKEL AG & CO. KGAA, Duesseldorf (DE); HENKEL IP & HOLDING GMBH, Duesseldorf (DE)

( * ) Notice: Subject to any disclaimer, the term of this patent is extended or adjusted under 35 U.S.C. 154(b) by 0 days.

(21) Appl. No.: 16/031,023

(22) Filed: Jul. 10, 2018

(65) Prior Publication Data
US 2018/0312532 A1 Nov. 1, 2018

Related U.S. Application Data

(63) Continuation of application No. PCT/CN2016/070609, filed on Jan. 11, 2016.

(51) Int. Cl.
| | |
|---|---|
| C08F 2/46 | (2006.01) |
| C08F 2/50 | (2006.01) |
| C08G 61/04 | (2006.01) |
| C07F 9/53 | (2006.01) |
| C07F 9/32 | (2006.01) |
| C08G 77/08 | (2006.01) |

(52) U.S. Cl.
CPC .......... *C07F 9/5337* (2013.01); *C07F 9/3252* (2013.01); *C08F 2/50* (2013.01); *C08G 77/08* (2013.01)

(58) Field of Classification Search
USPC ................ 522/64, 6, 71, 189, 184, 1; 520/1
See application file for complete search history.

(56) References Cited

U.S. PATENT DOCUMENTS

| | | |
|---|---|---|
| 4,273,907 A | 6/1981 | Takamizawa et al. |
| 4,391,963 A | 7/1983 | Shirahata |
| 4,536,265 A | 8/1985 | Fabrizio et al. |
| 5,776,658 A | 7/1998 | Niesert et al. |
| 6,399,805 B2 | 6/2002 | Wolf et al. |
| 6,627,672 B1 | 9/2003 | Lin et al. |
| 7,618,766 B2 | 11/2009 | Mutoh |
| 2010/0233601 A1* | 9/2010 | Takimoto ............ G03G 5/0575 430/56 |
| 2015/0116415 A1 | 4/2015 | Chretien et al. |
| 2015/0266907 A1 | 9/2015 | Li et al. |

FOREIGN PATENT DOCUMENTS

| | | |
|---|---|---|
| CN | 1200943 C | 5/2005 |
| CN | 102924509 A | 2/2013 |
| CN | 103333276 A | 10/2013 |
| EP | 1072326 A2 | 1/2001 |
| WO | 2016029439 A1 | 3/2016 |

OTHER PUBLICATIONS

De Groot, Jacqueline H. et al. "Hydrophilic Polymeric Acylphospine Oxide Photoinitiators/Crosslinkers for in Vivo Blue-Light Photopolymerization" Biomacromolecules, 2001 American Chemical Society, vol. 2, No. 4, pp. 1271-1278.

* cited by examiner

*Primary Examiner* — Jessica Whiteley
(74) *Attorney, Agent, or Firm* — Steven C. Bauman

(57) ABSTRACT

Certain phosphonate compounds useful as photoinitiators are provided herein.

28 Claims, No Drawings

SILICONE-COMPATIBLE COMPOUNDS

BACKGROUND

Field

The present invention relates to novel silicone-compatible compounds based on an α-hydroxy-alkylphenone moiety chemically bonded to a silicone, the production thereof by a simple reaction scheme, and their use as photoinitiators. The compounds of the invention absorb light in the longer ultraviolet light range (UVV) (i.e., wavelengths of about 390 nanometers or greater), which are not absorbed by the cover layers in optically clear display applications. The compounds of the invention are also clear and highly soluble in silicones. Hence, the compounds of the invention are particularly useful to initiate photocuring of compositions comprising silicones having unsaturated free-radical curable functional groups. Due to their remarkable stability the compounds of the invention do not give rise to hazing or yellowing and may be used for example in the preparation of optically clear silicone sealants and coatings and optically clear displays.

BRIEF DESCRIPTION OF RELATED TECHNOLOGY

Photoinduced polymerization of monomers or oligomers comprising functional groups prone to radical reactions is a widely used technique in the production of polymers. To initiate the reaction photoinitiators are usually added to the monomers or oligomers and the mixture is then exposed to electromagnetic radiation. Many photoinitiators are available that are readily soluble in unsaturated organic resins, and effectively cure these. However, many of these photoinitiators have poor solubility, and therefore unsatisfactory curing effectiveness, in silicones. Such photoinitiators separate from the silicone matrix during storage causing severe haze in any cured product produced. This is not acceptable if the products are intended to be used for optical clear display applications. In order to increase solubility in and hence compatibility with silicones it has been proposed to chemically bond the photoinitiators with organopolysiloxanes or silanes.

U.S. Pat. No. 4,273,907 discloses a novel class of organopolysiloxane compounds comprising at least one benzoin group chemically bonded to a silicon atom of the organopolysiloxane molecule. Such compounds may be prepared by the dehydrohalogenation, dehydrogenation, dehydration or dealkoholation condensation reaction between a corresponding organopolysiloxane having silicon-bonded halogen atoms, hydrogen atoms, hydroxyl groups or alkoxy groups and a benzoin compound in the presence of a suitable reaction promoter or a condensation catalyst. They are soluble in silicone compositions and useful as a photosensitizer in photocurable organopolysiloxane compositions. However, the compounds do not show sufficient stability and tend to cause yellowing upon exposure to heat and/or UV radiation over a longer period. Hence, they are not suitable to be used in high-performance transparent coatings, encapsulants or sealants.

U.S. Pat. No. 4,391,963 also discloses novel photosensitizers, being organopolysiloxane compounds bearing at least one chemically bonded benzoin group. Here, however, the compounds are prepared by hydrosilylation of an alkenyl-substituted benzoin and a silicon compound containing at least one silicon-bonded hydrogen atom. Hence, the organopolysiloxane moiety and the benzoin group are bonded via a divalent hydrocarbon group. This results in an increased stability against hydrolysis, however, requires a comparatively elaborate preparation process since alkenyl-substituted benzoins are not readily available, but have to be synthesized in a separate reaction step.

From U.S. Pat. No. 4,536,265 also discloses organopolysiloxane photoinitiators. At least one siloxane unit per molecule comprises an acetophenone photomoiety bonded to the silicon atom of the siloxane unit via a divalent hydrocarbon group having between 2 and 10 carbon atoms. Such a binding group shows high stability against hydrolysis. However, alkenyl-substituted acetophenones are not readily available, but must be synthesized in a separate reaction step, making the overall process to produce the organopolysiloxane photoinitiators complex. Moreover, acetophenone moieties tend to cause yellowing upon exposure to heat and/or UV radiation over a longer period.

U.S. Pat. No. 5,776,658 describes silicone-compatible photoinitiators comprising a silane or organopolysiloxane residue bearing a chemically bonded radical of a compound that has one or more of a photoinitiator or photosensitizer activity and that has at least one carbonyl group located on an aromatic nucleus. Again, the bonding of the silane or organopolysiloxane residue and the photomoiety is effected via a divalent hydrocarbon group. This divalent hydrocarbon group is attached to an aromatic carbon atom which is positioned ortho to the carbonyl group of the photomoiety. The photoinitiators show good stability against hydrolysis. The examples disclose preparation of the photoinitiators via a one-pot reaction. However, the resulting product mixture needs to be concentrated and worked up by chromatography. So the overall process is complex and time-consuming. Moreover, the yields of photoinitiator are rather low, e.g. only 17% in example 5.

EP 1072326 A2 provides siloxane-containing surface-active photoinitiators that concentrate on the surface of the formulation. These photoinitiators are used in a method for producing scratch-resistant coatings from formulations containing ethylenic compounds. The photomoiety comprises an aromatic ring which is linked via a bridging unit (Y) to a silicon atom of the siloxane residue. Due to the surface-active properties of these photoinitiators they will not be homogeneously distributed throughout the formulation and, thus, are not suitable for high-performance transparent coatings, encapsulants, or sealants.

U.S. Pat. Appln. Pub. No. 2015/0266907 provides silicone-compatible photoinitiators that are produced from readily available starting materials via a simple one-step reaction. These photoinitiators are highly soluble in photocurable silicones and stable against thermal stress, UV radiation, and hydrolysis to avoid yellowing of any cured product. However, these photoinitiators absorb in light in the shorter ultraviolet light range (i.e., wave lengths less than 390 nanometers). The cover layers of optically clear displays may interfere with the transmission of these shorter wavelengths to the photocurable silicones situated between the cover layers. Accordingly, these photoinitiators may be less effective in promoting the curing of photocurable silicones when used in optically clear display applications.

It would be advantageous to make and use compounds that are clear and highly soluble in photocurable silicones and stable against thermal stress, UV radiation, and hydrolysis to avoid hazing and yellowing of the cured product, and for which ultraviolet wavelengths of about 390 nanometers or greater are effective in initiating curing of the photocurable silicones.

SUMMARY

The present invention provides novel compounds, which may act as silicone-compatible photoinitiators, accessible from readily available starting materials via a simple reaction scheme. They are clear and highly soluble in photocurable silicones and stable against thermal stress, UV radiation, and hydrolysis to avoid hazing and yellowing of any cured product including such photoinitiators. Moreover, the compounds of the invention produce no small molecule by-products during curing due to the inclusion of the silicone side chains. Thus, the compounds of the invention do not contribute to hazing and yellowing of the cured product. Such compounds are particularly useful, for example, as photoinitiators in the production of optically clear displays.

The cover layers of optically clear displays often absorb shorter wavelengths of ultraviolet light (i.e., wavelengths less than 390 nanometers). However, the novel silicone-compatible compounds of the present invention absorb longer wavelengths of ultraviolet light (UVV) (i.e., wavelengths of about 390 nanometers or greater). Accordingly, this additional property makes the compounds of the present invention particularly useful as photoinitiators in the production of optically clear displays.

The inventors found that specific compounds based on α-hydroxy-alkylphenone photomoieties bonded at the phenyl group to a silicone side chain provide the desired properties.

In one aspect of the invention there is provided a compound represented by the following Formula I:

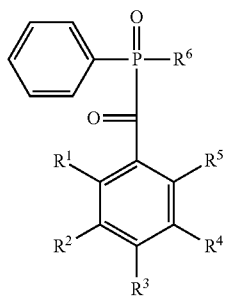

I wherein:
$R^1$, $R^2$, $R^3$, $R^4$, and $R^5$ are the same or different and are selected from the group consisting of $SIL_1$-X, hydrogen, $C_1$-$C_{20}$ alkyl, $C_2$-$C_8$ alkenyl, $C_5$-$C_8$ cycloalkyl, phenyl $C_1$-$C_3$ alkyl, and fluorine;

X is optional, and if present is $C_1$-$C_{12}$ alkyl;

$SIL_1$ has the general formula:

$(R^7SiO_{3/2})_a(R^7_2SiO_{2/2})_b(R^7_3SiO_{1/2})_c$ wherein:
$R^7$ is selected from the group consisting of $C_1$-$C_{20}$ alkyl, $C_2$-$C_8$ alkenyl, $C_5$-$C_8$ cycloalkyl, alkoxyl, phenyl, and phenyl $C_1$-$C_3$ alkyl;
a is a positive number,
b is 0 or a positive number,
c is 0 or a positive number,
b/a is from 0 to 100, and
c/a is from 0 to 10,
wherein at least one of $R^1$, $R^2$, $R^3$, $R^4$, and $R^5$ is $SIL_1$-X; and $R^6$ is selected from the group consisting of $C_1$-$C_{20}$ alkyl, $C_2$-$C_8$ alkenyl, $C_5$-$C_8$ cycloalkyl, phenyl, phenyl $C_1$-$C_3$ alkyl, trimethylphenol, and fluorine.

In another aspect of the invention there is provided a method of synthesizing a compound represented by the following Formula I:

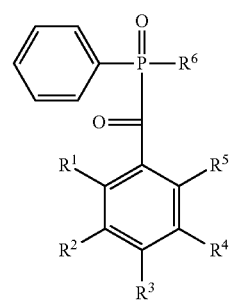

I wherein:
$R^1$, $R^2$, $R^3$, $R^4$, and $R^5$ are the same or different and are selected from the group consisting of $SIL_1$-X, hydrogen, $C_1$-$C_{20}$ alkyl, $C_2$-$C_8$ alkenyl, $C_5$-$C_8$ cycloalkyl, phenyl $C_1$-$C_3$ alkyl, and fluorine;

X is optional, and if present is $C_1$-$C_{12}$ alkyl;

$SIL_1$ has the general formula:

$(R^7SiO_{3/2})_a(R^7_2SiO_{2/2})_b(R^7_3SiO_{1/2})_c$ wherein:
$R^7$ is selected from the group consisting of $C_1$-$C_{20}$ alkyl, $C_2$-$C_8$ alkenyl, $C_5$-$C_8$ cycloalkyl, alkoxyl, and phenyl $C_1$-$C_3$ alkyl;
a is a positive number,
b is 0 or a positive number,
c is 0 or a positive number,
b/a is from 0 to 100, and
c/a is from 0 to 10,
wherein at least one of $R^1$, $R^2$, $R^3$, $R^4$, and $R^5$ is $SIL_1$-X; and $R^6$ is selected from the group consisting of $C_1$-$C_{20}$ alkyl, $C_2$-$C_8$ alkenyl, $C_5$-$C_8$ cycloalkyl, phenyl, phenyl $C_1$-$C_3$ alkyl, trimethylphenol, and fluorine, comprising the steps of:
1) Activating a compound of Formula A:

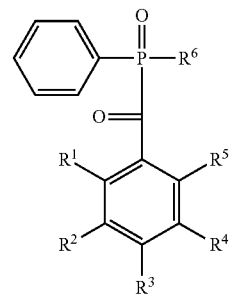

A wherein $R^1$, $R^2$, $R^3$, $R^4$, and $R^5$ are as above, but none may be $SIL_1$-X, to produce a compound of Formula B:

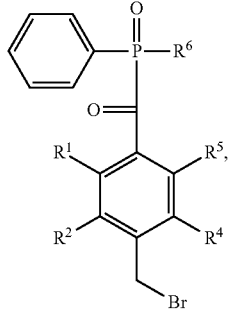

2) Subjecting the compound of Formula B to a nucleophilic acetate substitution reaction to produce a compound of Formula C:

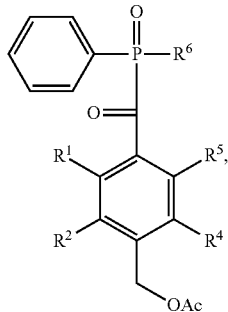

3) Subjecting the compound of Formula C to a hydrolysis reaction to produce a compound of Formula D:

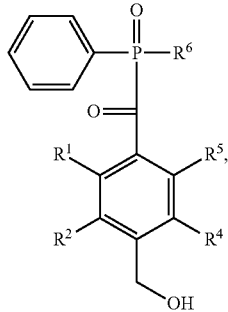

and

4) Subjecting the compound of Formula D to a condensation reaction with a compound having the formula $SIL_1$-X—Cl or $SIL_1$-X—H to produce the compound of Formula 1.

In a further aspect of the invention there is provided a composition comprising:

a) about 70 to about 99.9 weight percent of a photocurable silicone; and b) about 0.1 to about 10.0 weight percent of a compound represented by the following Formula I:

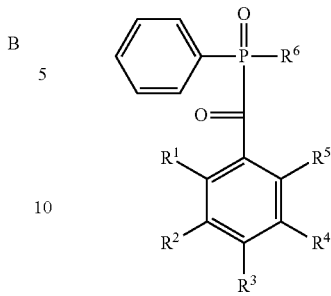

wherein:
$R^1$, $R^2$, $R^3$, $R^4$, and $R^5$ are the same or different and are selected from the group consisting of $SIL_1$-X, hydrogen, $C_1$-$C_{20}$ alkyl, $C_2$-$C_8$ alkenyl, $C_5$-$C_8$ cycloalkyl, phenyl $C_1$-$C_3$ alkyl, and fluorine;
X is optional, and if present is $C_1$-$C_{12}$ alkyl;
$SIL_1$ has the general formula:

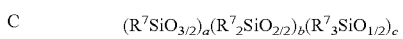

wherein:
$R^7$ is selected from the group consisting of $C_1$-$C_{20}$ alkyl, $C_2$-$C_8$ alkenyl, $C_5$-$C_8$ cycloalkyl, alkoxyl, phenyl, and phenyl $C_1$-$C_3$ alkyl;
a is a positive number,
b is 0 or a positive number,
c is 0 or a positive number,
b/a is from 0 to 100, and
c/a is from 0 to 10,
wherein at least one of $R^1$, $R^2$, $R^3$, $R^4$, and $R^5$ is $SIL_1$-X; and
$R^6$ is selected from the group consisting of $C_1$-$C_{20}$ alkyl, $C_2$-$C_8$ alkenyl, $C_5$-$C_8$ cycloalkyl, phenyl, phenyl $C_1$-$C_3$ alkyl, trimethylphenol, and fluorine.

In another aspect of the invention there is provided a method of making a silicone polymer product, comprising the steps of:

A) Providing a photocurable silicone composition comprising:
 i) about 70 to about 99.9 weight percent of a photocurable silicone; and
 ii) about 0.1 to about 10.0 weight percent of a compound represented by the following Formula I:

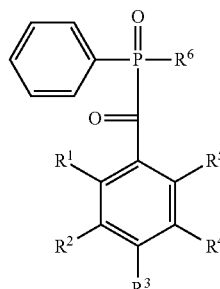

wherein:
$R^1$, $R^2$, $R^3$, $R^4$, and $R^5$ are the same or different and are selected from the group consisting of $SIL_1$-X, hydrogen, $C_1$-$C_{20}$ alkyl, $C_2$-$C_8$ alkenyl, $C_5$-$C_8$ cycloalkyl, phenyl $C_1$-$C_3$ alkyl, and fluorine;

X is optional, and if present is $C_1$-$C_{12}$ alkyl;

$SIL_1$ has the general formula:

wherein:

$R^7$ is selected from the group consisting of $C_1$-$C_{20}$ alkyl, $C_2$-$C_8$ alkenyl, $C_5$-$C_8$ cycloalkyl, alkoxyl, phenyl, and phenyl $C_1$-$C_3$ alkyl;

a is a positive number, b is 0 or a positive number, c is 0 or a positive number, b/a is from 0 to 100, and c/a is from 0 to 10, wherein at least one of $R^1$, $R^2$, $R^3$, $R^4$, and $R^5$ is $SIL_1$-X; and $R^6$ is selected from the group consisting of $C_1$-$C_{20}$ alkyl, $C_2$-$C_8$ alkenyl, $C_5$-$C_8$ cycloalkyl, phenyl, phenyl $C_1$-$C_3$ alkyl, trimethylphenol, and fluorine; and B) Exposing the photocurable silicone composition to ultraviolet radiation or visible light to initiate photocuring of the photocurable silicone composition to produce the silicone polymer product.

DETAILED DESCRIPTION

The compounds according to the invention may be used as photoinitiators and are particularly effective if used in compositions based on photocurable silicones.

The $SIL_1$-X group in the compound of the present invention is represented by the formula:

wherein $R^7$ is a $C_1$-$C_{20}$ alkyl, $C_2$-$C_8$ alkenyl, $C_5$-$C_8$ cycloalkyl, alkoxyl, phenyl, or phenyl $C_1$-$C_3$ alkyl group. Moreover, a is a positive number, b is 0 or a positive number, c is 0 or a positive number, b/a is from 0 to 100, and c/a is from 0 to 10. X is optional, and if present is a $C_1$-$C_{12}$ alkyl group.

Preferably, X is not present, $R^7$ is a methyl group or a methoxy group, a is 1, b is 0, and c is 2 or 3.

The compounds of the present invention may contain up to 5 $SIL_1$-X groups, one each at $R_1$ through $R_5$. Preferably, the compounds of the present invention contain 1, 2, or 3 $SIL_1$-X groups at one or more of $R^1$, $R^2$, or $R^3$. In one embodiment, compounds of the present invention contain a single $SIL_1$-X group at $R^3$. Preferably, if not occupied by a $SIL^1$-X group, $R^1$ and $R^5$ are methyl groups and $R^2$ and $R^4$ are hydrogen.

The compounds according to the invention show advantageous properties if $R_3$ is $SIL_1$-X and the $SIL_1$-X is:

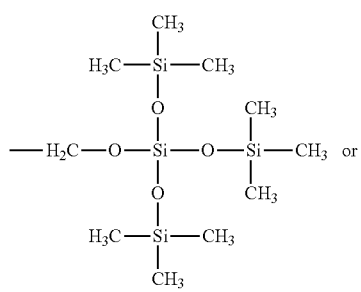

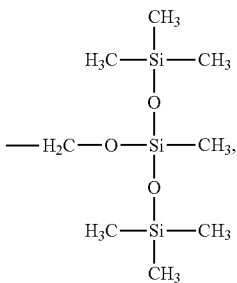

$R^1$ and $R^5$ are methyl groups, and $R^2$ and $R^4$ are hydrogen.

$R^6$ is a $C_1$-$C_{20}$ alkyl group, a $C_2$-$C_8$ alkenyl group, a $C_5$-$C_8$ cycloalkyl group, a phenyl group, a phenyl $C_1$-$C_3$ alkyl group, a trimethylphenol group, or fluorine. Preferably, $R^6$ is a phenyl group, $CH_3CH_2O$—, or a trimethylphenol group.

The compounds according to the invention show particularly advantageous properties if $R_3$ is $SIL_1$-X and the $SIL_1$-X is:

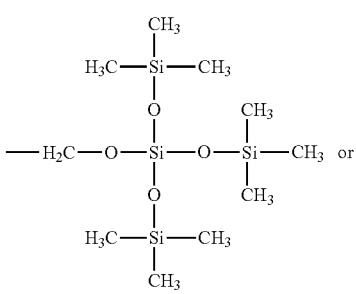

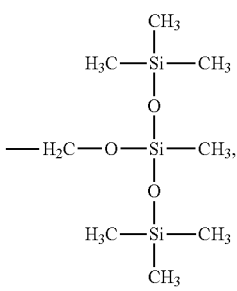

$R^1$ and $R^5$ are methyl groups, $R^2$ and $R^4$ are hydrogen, and $R_6$ is a phenyl group, $CH_3CH_2O$—, or a trimethylphenol group.

Preferably, the compound of the present invention is one of the following:

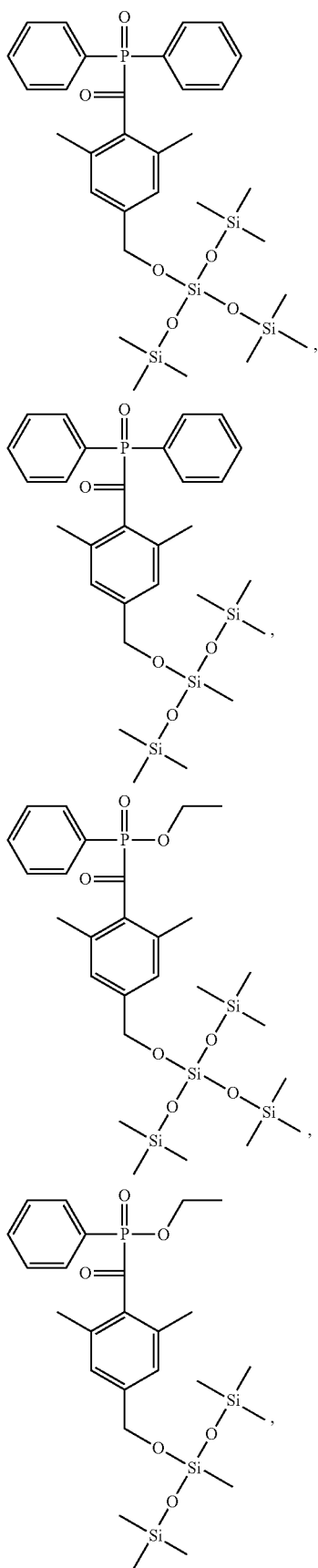

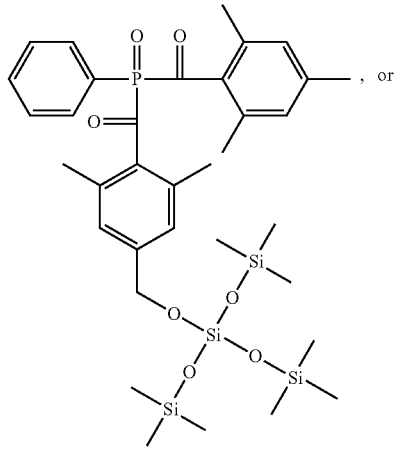

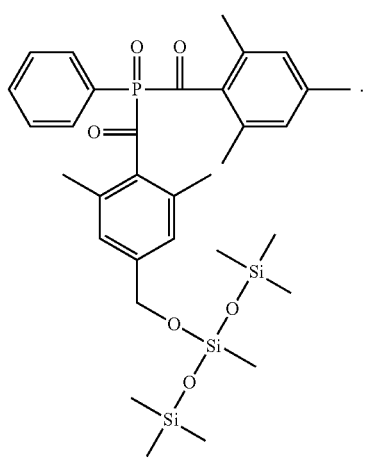

These compounds may be employed alone or in combination in the compositions and methods of the present invention.

The compounds of the present invention may be synthesized through a customizable four-step process to allow for diversity in the possible silicone-compatible photoinitiators that may be produced. The four steps of the synthesis may generally described as follows:

Step 1) The phenyl group of the α-hydroxy-alkylphenone starting material is activated by addition of a bromine to the phenyl group though electrophilic halogenation;

Step 2) The bromine is then substituted with acetate by a nucleophilic acetate substitution reaction;

Step 3) The acetate is then hydrolyzed to a hydroxy group through a hydrolysis reaction; and Step 4) The silicone side chain is then attached to the phenyl group of the α-hydroxy-alkylphenone through a condensation reaction to produce the compound of the invention.

The reaction scheme for synthesis of the compounds of the present invention may be generally represented as follows:

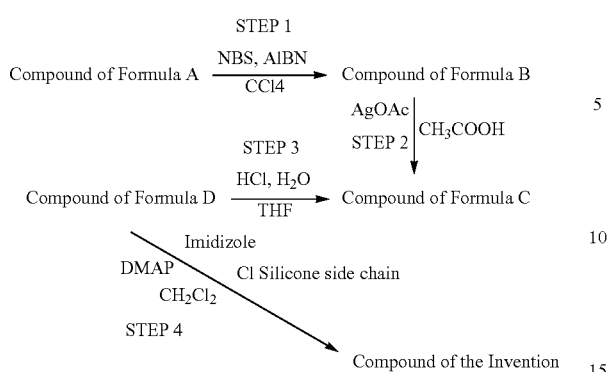

The preferred general parameters for the synthesis of the compounds of the present invention are shown in Table 1.

TABLE 1

| Step | Parameter | Preferred Range | More Preferred Range |
|---|---|---|---|
| Step 1 Bromized Reaction | Ratio of starting material to N-bromosuccinimide (NBS) | 0.1-100 | 0.8-1.2 |
| | Temperature | 20-200° C. | 50-150° C. |
| Step 2 Nucleophilic Substitution Reaction | Ratio of Compound of Formula B to silver acetate(AgOAc) | 0.1-100 | 0.8-1.2 |
| | Temperature | 20-220° C. | 50-150° C. |
| Step 3 Hydrolysis Reaction | Molar ratio of acetate to water | 0.1-100 | 0.8-1.2 |
| | Temperature | 20-220° C. | 50-150° C. |
| Step 4 Condensation Reaction | Molar ratio of hydroxyl ketone to CH$_3$- or Cl-silicone side chain | 0.1-100 | 0.8-1.2 |
| | Temperature | 20-220° C. | 50-150° C. |

Desirably, starting materials for the synthesis of the compounds of the present invention are α-hydroxy-alkylphenones, examples of which may be represented by the compound of Formula A:

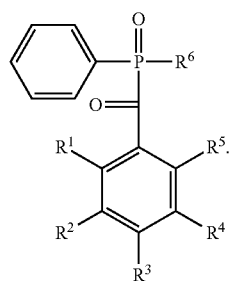

A in which $R^1$, $R^2$, $R^3$, $R^4$, and $R^5$ are the same as in the compounds of the present invention (as described above), but none may be $SIL_1$-X, and $R^6$ is the same as in the compounds of the present invention.

Preferably, $R^1$, $R^2$, $R^3$, $R^4$, and $R^5$ are independently hydrogen or methyl groups. In preferred starting materials $R^1$, $R^3$, and $R^5$ are methyl groups and $R^2$ and $R^4$ are hydrogen. Preferably, $R_6$ is a phenyl group, CH$_3$CH$_2$O—, or a trimethylphenol group in the starting material.

Preferred starting materials include the following compounds:

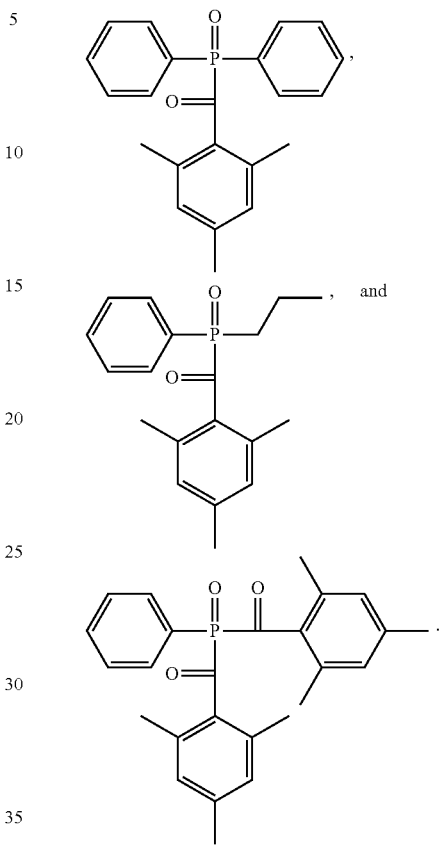

A further aspect of the invention is the use of these compounds as photoinitiators. A particular aspect of the invention is a method of using the compounds according to the invention as photoinitiators including the steps of mixing the compound with a photocurable silicone, such as a photopolymerizable organopolysiloxane or silicone resin, and exposing the resulting mixture to electromagnetic radiation.

Although there is no particular limitation regarding the photocurable silicone, it is preferred to add the compound according to the invention to a composition based solely or predominately on (meth)acryloxysiloxanes, e.g., (meth)acrylic endcapped silanol terminated polydimethylsiloxane, since photocuring such mixtures results in products having a degree of haze of less than about 2, preferably less than about 1, a degree of yellowing of less than about 2, preferably less than about 1, and showing very good thermal, hydrolytic, and UV stability. Preferably, the photocurable silicone is an organopolysiloxane or silicone resin, a (meth)acrylic endcapped silicone, a (meth)acryloxysiloxane, or a (meth)acrylic endcapped silanol terminated polydimethylsiloxane.

Useful electromagnetic radiation is any radiation that will provoke forming of radicals and, hence, start free-radical polymerization of the photocurable silicone. An example of such electromagnetic radiation is UVV radiation (ultraviolet light at wavelengths of about 390 nanometers or greater).

A further aspect of the invention is a composition comprising: a) at least one photocurable silicone and b) a compound according to the invention. Preferably, the photocurable silicone is an organopolysiloxane or silicone resin, a (meth)acrylic endcapped silicone, a (meth)acryloxysiloxane, or a (meth)acrylic endcapped silanol terminated polydimethylsiloxane. Preferred photocurable silicones include ultraviolet curable organosilicones and ultraviolet and moisture dual cure silicones.

The amount of the compound according to the invention in such compositions may vary within broad limits. Preferably, the composition of the invention comprises the compound according to the invention or a mixture of several compounds according to the invention in a total amount of 0.1 to 30% by weight, preferably 0.2 to 15% by weight, more preferably 0.5 to 10% by weight, based on the weight of the composition. The remainder generally consists solely or predominantly of the photocurable silicone.

Yet another aspect of the invention is method of making a silicone polymer product by exposing a composition including a) at least one photocurable silicone and b) a compound according to the invention to electromagnetic radiation to initiate photocuring to produce the silicone polymer product. Preferably, the electromagnetic radiation is UVV radiation (ultraviolet light at wavelengths of about 390 nanometers or greater), more preferably ultraviolet radiation at a wavelength of about 405 nanometers.

In preferred embodiments, the method of making a silicone polymer product includes the further step of placing the photocurable silicone composition in contact with at least one layer of an optically clear composition prior to the initiation of photocuring. Thus, when the photocurable silicone composition is cured, the silicone polymer product is suitable for use in an optically clear display. Preferably, the method of making a silicone polymer product of the invention includes the step of placing the photocurable silicone composition between two layers of an optically clear composition prior to the initiation of photocuring.

Optically clear compositions for use in the methods of the invention include any material which provides a transmittance of visible light of greater than about 95%, preferably greater than about 98%, even more preferably greater than about 99%. Preferably, the optically clear composition is glass.

Preferably, the polymer products of the invention exhibit excellent clarity and maintain such clarity even in the face of long periods of aging. Preferably, the silicone polymer products of the invention have a haze value of about 2 or less, more preferably about 1 or less, and a yellowness value of about 2 or less, more preferably about 1 or less, at a gap of 750 micrometers between layers of optically clear composition, when aged for 500 hours in a QUV test machine or when aged for 500 hours in an oven at 85° C. and 85% relative humidity. Preferably, the silicone polymer products of the invention provide a transmittance of visible light of greater than about 95%, preferably greater than about 98%, even more preferably greater than about 99%.

Below is a description of particular aspects of the present invention using a series of examples, however, the present invention is in no way restricted to the below presented examples.

EXAMPLES

Synthesis Example 1

Step 1:

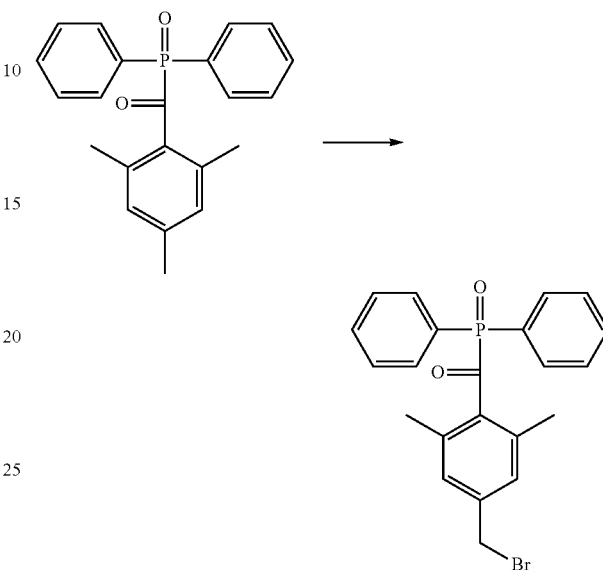

A mixture of Darocur TPO (17.5 g, 50.3 mmol), N-bromosuccinimide (12.5 g, 70.4 mmol), AIBN (201 mg), and tetrachloromethane (100 ml) was charged into a 250 ml three-necked flask and refluxed at 80° C. for 5 hours under argon. The reaction mixture was filtered after cooling. The filtrate was evaporated to obtain a crude product.

Step 2:

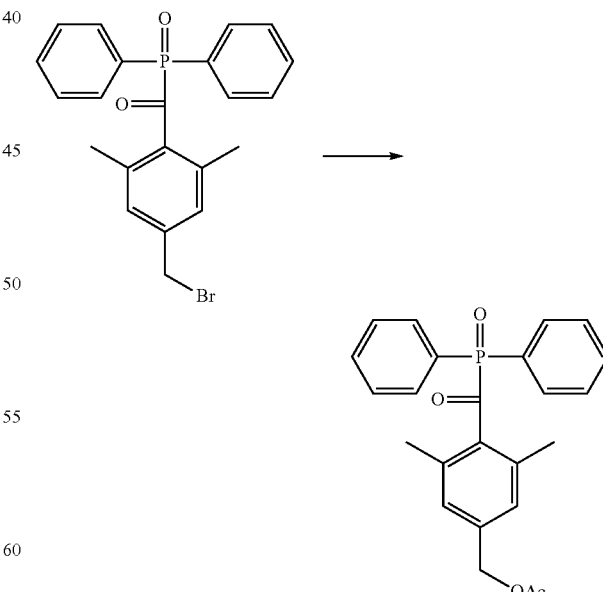

A mixture of the crude product of STEP 1 (without further purification), silver acetate (10.07 g, 60.35 mmol), and 150 ml glacial acetic acid was charged into a 500 ml three-necked flask and refluxed at 100° C. for 3 hours under argon.

The mixture was filtered and 500 ml of water was added to the filtrate. The resulting mixture was extracted with CH$_2$Cl$_2$ (50 ml) 3 times. The combined organic layer was washed with 50 ml of water, dried over anhydrous Na$_2$SO$_4$, and the solvent removed under reduced pressure. The crude product was purified by column chromatography (50% EtOAc in hexane) to produce 7.4 g of intermediate compound (36% yield for combined STEPS 1 and 2).

Step 3:

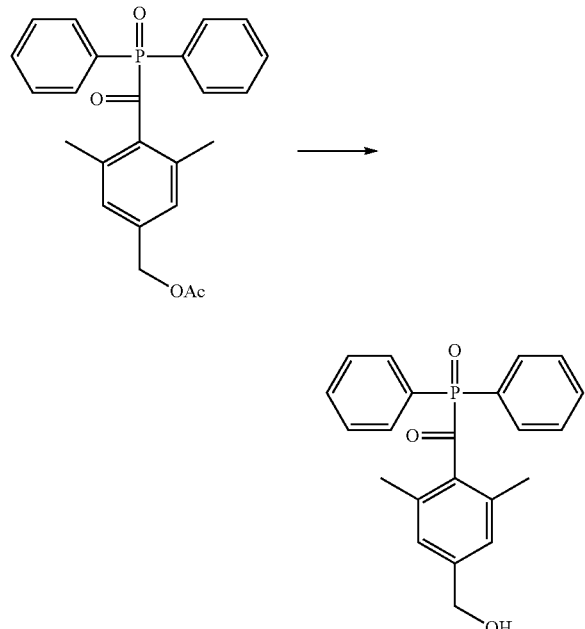

A mixture of the purified intermediate of STEP 2 (7.4 g, 18.2 mmol), THF (44 ml), HCl (10.5 ml), and water (52 ml) was charged into a 250 ml three-necked flask and refluxed at 80° C. overnight under argon. The THF was removed under reduced pressure and 15 ml of water was added. The resulting mixture was extracted with CH$_2$Cl$_2$ (30 ml) 3 times. The combined organic layer was washed with 10 ml of water. The organic layer was then dried over anhydrous Na$_2$SO$_4$, and the solvent was evaporated. This crude product (9.1 g, yellow solid) was used in the next step without further purification.

Step 4:

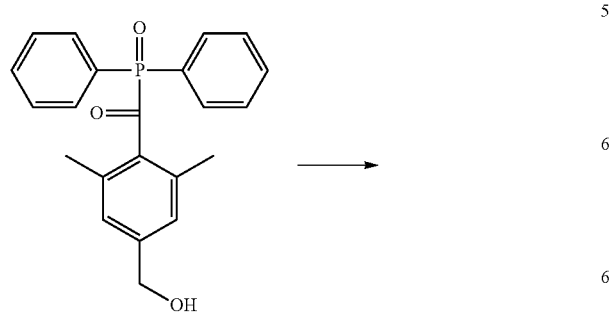

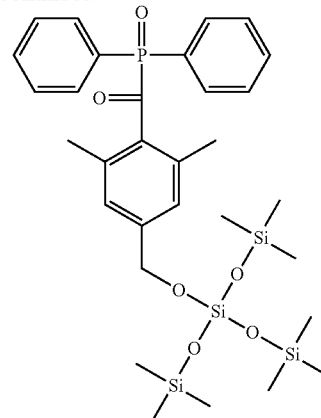

A solution of the crude product of STEP 3 (9 g, 24.7 mmol), imidazole (3.36 g, 49.4 mmol), and DMAP (40 mg) in CH$_2$Cl$_2$ (100 ml) was charged into a 250 ml three-necked flask and ClSi(CH$_3$SiO)$_3$ (9.82 g, 29.63 mmol) was added. The mixture was stirred at room temperature overnight under argon. The reaction was quenched by addition of water. The aqueous phase was extracted with CH$_2$Cl$_2$ (20 ml) 3 times. The combined organic phase was washed with water and brine. The organic phase was dried with anhydrous Mg$_2$SO$_4$. After solvent removal under reduced pressure, the residue was purified by column chromatography to produce 10.98 g of the compound of the invention (67% yield, light yellow solid).

Synthesis Example 2

Step 1:

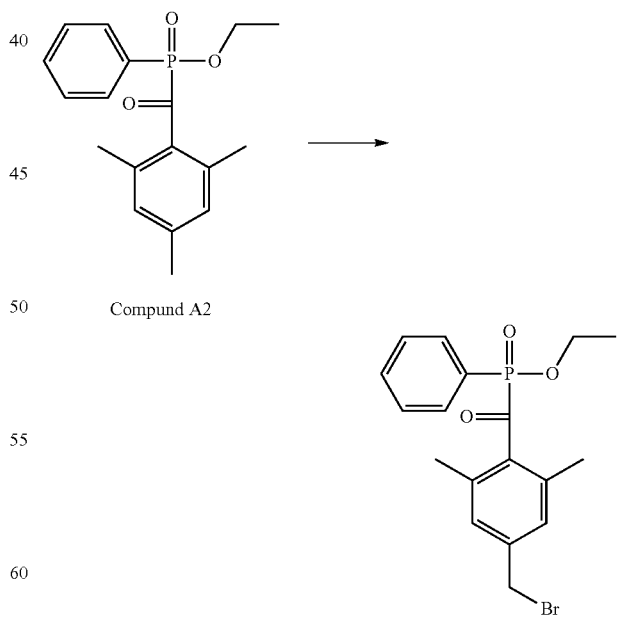

A mixture of Compound A2 (above) (12.65 g, 40.0 mmol), N-bromosuccinimide (8.54 g, 48.0 mmol), AIBN (160.0 mg), and tetrachloromethane (80 ml) was charged into a 250 ml three-necked flask and refluxed at 80° C. for 5 hours under argon. The reaction mixture was filtered after cooling. The filtrate was evaporated to obtain a crude product.

Step 2:

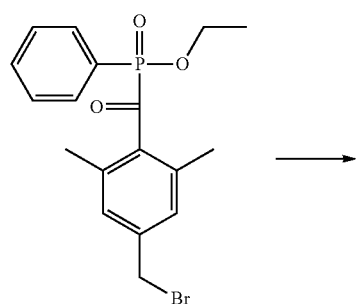

A mixture of the crude product of STEP 1 (without further purification), silver acetate (8.01 g, 48.0 mmol), and 100 ml glacial acetic acid was charged into a 250 ml three-necked flask and refluxed at 120° C. for 3 hours under argon. The mixture was filtered and 500 ml of water was added to the filtrate. The resulting mixture was extracted with $CH_2Cl_2$ (50 ml) 3 times. The combined organic layer was washed with 50 ml of water, dried over anhydrous $Na_2SO_4$, and the solvent removed under reduced pressure. The crude product was purified by column chromatography (50% EtOAc in hexane) to produce 6.18 g of intermediate compound (41% yield for combined STEPS 1 and 2).

Step 3:

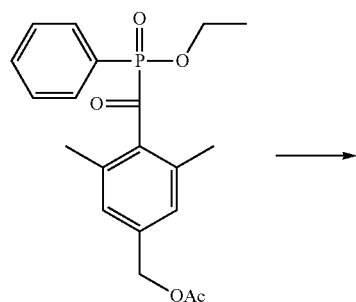

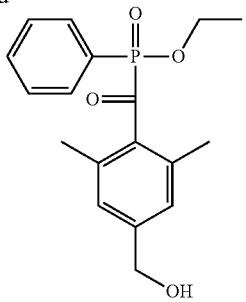

A mixture of the purified intermediate of STEP 2 (6.18 g, 16.5 mmol), THF (40 ml), HCl (9.5 ml), and water (47 ml) was charged into a 250 ml three-necked flask and refluxed at 80° C. overnight under argon. The THF was removed under reduced pressure and 15 ml of water was added. The resulting mixture was extracted with $CH_2Cl_2$ (30 ml) 3 times. The combined organic layer was washed with 10 ml of water. The organic layer was then dried over anhydrous $Na_2SO_4$, and the solvent was evaporated. This crude product (4.8 g, yellow liquid) was used in the next step without further purification.

Step 4:

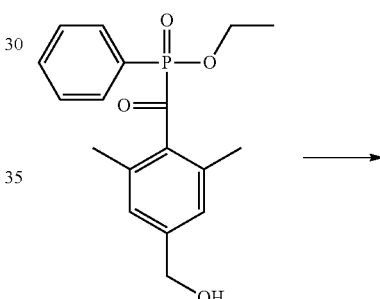

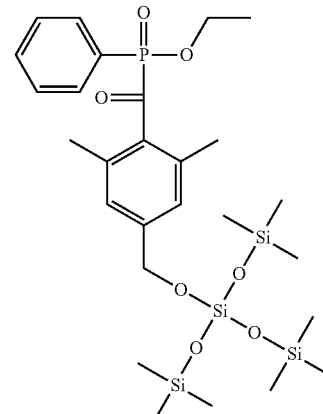

A solution of the crude product of STEP 3, imidazole (2.24 g 33.5 mmol), DMAP (25 mg) in $CH_2Cl_2$ (60 ml) was charged into a 250 ml three-necked flask and $ClSi(CH_3SiO)_3$ (8.2 g, 27.4 mmol) was added. The mixture was stirred at room temperature overnight under argon. The reaction was quenched by addition of water. The aqueous phase was extracted with $CH_2Cl_2$ (20 ml) 3 times. The combined organic phase was washed with water and brine. The organic phase was dried with anhydrous $Mg_2SO_4$. After solvent removal under reduced pressure, the residue was purified by column chromatography (20% EtOAc in hexane) to produce 4.76 g of the compound of the invention (45% yield, light yellow liquid).

Synthesis Example 3

Step 1:

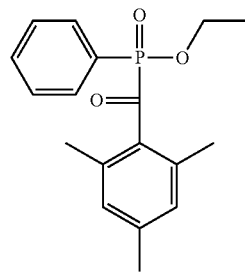

Compund A2

A mixture of Compound A2 (above)(12.65 g, 40.0 mmol), N-bromosuccinimide (8.54 g, 48.0 mmol), AIBN (160.0 mg), and tetrachloromethane (80 ml) was charged into a 250 ml three-necked flask and refluxed at 80° C. for 5 hours under argon. The reaction mixture was filtered after cooling. The filtrate was evaporated to obtain a crude product.

Step 2:

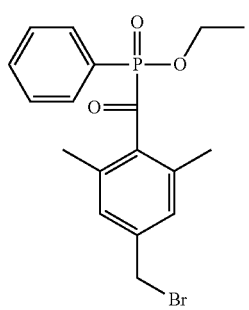

A mixture of the crude product of STEP 1 (without further purification), silver acetate (8.01 g, 48.0 mmol), and 100 ml glacial acetic acid was charged into a 250 ml three-necked flask and refluxed at 120° C. for 3 hours under argon. The mixture was filtered and 500 ml of water was added to the filtrate. The resulting mixture was extracted with $CH_2Cl_2$ (50 ml) 3 times. The combined organic layer was washed with 50 ml of water, dried over anhydrous $Na_2SO_4$, and the solvent removed under reduced pressure. The crude product was purified by column chromatography (50% EtOAc in hexane) to produce 6.18 g of intermediate compound (41% yield for combined STEPS 1 and 2).

Step 3:

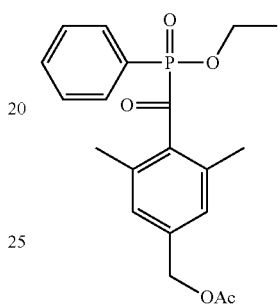

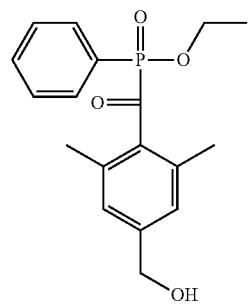

A mixture of the purified intermediate of STEP 2 (6.18 g, 16.5 mmol), THF (40 ml), HCl (9.5 ml), and water (47 ml) was charged into a 250 ml three-necked flask and refluxed at 80° C. overnight under argon. The THF was removed under reduced pressure and 15 ml of water was added. The resulting mixture was extracted with $CH_2Cl_2$ (30 ml) 3 times. The combined organic layer was washed with 10 ml of water. The organic layer was then dried over anhydrous $Na_2SO_4$, and the solvent was evaporated. This crude product (4.8 g, yellow liquid) was used in the next step without further purification.

Step 4:

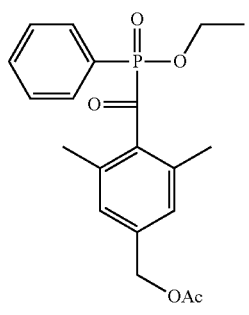

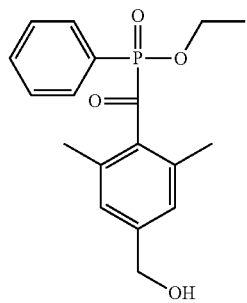

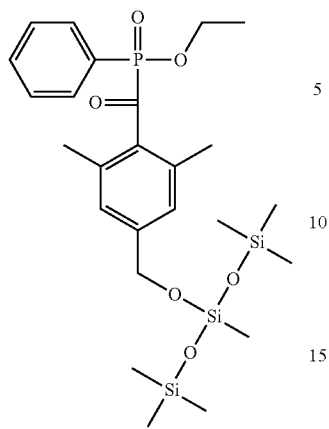

A solution of the crude product of STEP 3 (3.0 g, 9.0 mmol), imidazole (1.36 g, 20.0 mmol), and DMAP (20 mg) in Toluene (40 ml) was charged into a 250 ml three-necked flask and (CH$_3$SiO)$_2$SiCH$_3$H (18.0 mmol) was added. The mixture was stirred at room temperature overnight under argon. The reaction was quenched by addition of water (30 ml). The aqueous phase was extracted with CH$_2$Cl$_2$ (30 ml) 3 times. The combined organic phase was washed with water and brine. The organic phase was dried with anhydrous Mg$_2$SO$_4$. After solvent removal under reduced pressure, the residue was purified by column chromatography (PE:EA=5:1) to produce 3.55 g of the compound of the invention (71% yield, light yellow liquid).

Example 4

Evaluation of Photoinitiators

The compounds of Examples 2 and 3 above and comparative photoinitiators Darocur TPO and SPI-7 were evaluated for applicable cure initiation source, UV resistance, anti-yellowing, and anti-haze properties. Darocur TPO is a photoinitiator that is known for use with UVV radiation for curing. SPI-7 is a silicone substituted UVA photoinitiator. The structure of each of the compounds is shown below.

Compound of Example 2:

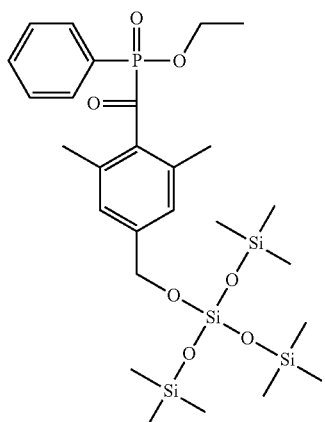

Compound of Example 3:

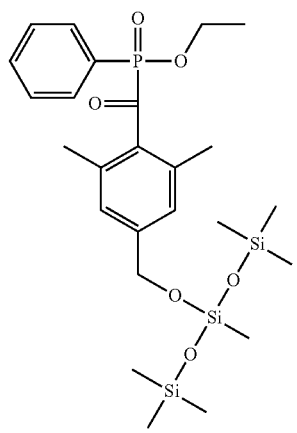 [SMILES: CCOP(=O)(C(=O)c1c(C)cc(CO[Si](C)(O[Si](C)(C)C)O[Si](C)(C)C)cc1C)c1ccccc1]

Darocur TPO:

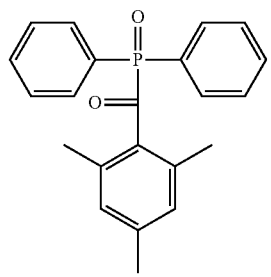 [SMILES: Cc1cc(C)c(C(=O)P(=O)(c2ccccc2)c2ccccc2)c(C)c1]

SPI-7:

The substrate used was acrylate silicone matrix (15MDMA:60DMA=6.4). The photoinitiators were each separately mixed with the substrate. These mixtures were then placed between 2 layers of glass separated by 750 micrometers and exposed to ultraviolet light. Initiation of curing was evaluated with UV radiation using the medium pressure mercury arch (MPMA) System UV chamber for 30 seconds at 75 mW/cm$^2$ twice to produce curing. Separately, initiation of curing was also evaluated using a 405 nanometer LED light source.

After curing, the samples were aged in a QUV test machine for 500 hours. After aging, hazing and yellowing for each sample were measured using a Datacolor 650 apparatus, available from Datacolor Corporation, in compliance with ASTM D1003 Standard Test Method.

The light source(s) capable of initiating curing and the results for hazing and yellowing are reported in Table 2.

TABLE 2

| Photoinitiator | Light Source(s) Capable of Initiating Curing | Hazing Value | Yellowing Value (b) |
|---|---|---|---|
| Darocur TPO | MPMA & 405 nm | 7.1 | 0.98 |
| Example 2 | MPMA & 405 nm | 0.1 | 0.60 |
| SPI-7 | MPMA | 0.1 | 0.33 |
| Example 3 | MPMA & 405 nm | 0.2 | 1.60 |

Hazing and yellowing values were determined at a gap of 750 micrometers. Hazing and yellowing values of about 2 or less were considered acceptable, and values of about 1 or less were considered excellent.

Based on the results reported in the Table 2, only the compounds of the invention produced acceptable hazing and yellowing values and could initiate curing using 405 nm ultraviolet light. The compound of Example 2 showed excellent values for both hazing and yellowing. Darocur TPO, which is free of silicone side chains, produced unacceptable hazing upon aging, and curing could not be initiated using 405 nm ultraviolet light with SPI-7.

The invention claimed is:

1. A photoinitiator of the general Formula I:

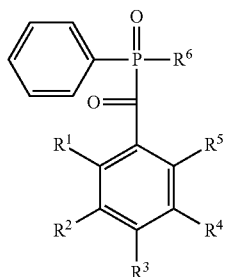

wherein:
R$^1$, R$^2$, R$^3$, R$^4$, and R$^5$ are the same or different and are selected from the group consisting of SIL$_1$-X, hydrogen, C$_1$-C$_{20}$ alkyl, C$_2$-C$_8$ alkenyl, C$_5$-C$_8$ cycloalkyl, phenyl C$_1$-C$_3$ alkyl, and fluorine;
X is optional, and if present is C$_1$-C$_{12}$ alkyl;
SIL$_1$ has the general formula:

$(R^7SiO_{3/2})_a(R^7{}_2SiO_{2/2})_b(R^7{}_3SiO_{1/2})_c$ wherein:
R$^7$ is selected from the group consisting of C$_1$-C$_{20}$ alkyl, C$_2$-C$_8$ alkenyl, C$_5$-C$_8$ cycloalkyl, alkoxyl, phenyl, and phenyl C$_1$-C$_3$ alkyl;
a is a positive number,
b is 0 or a positive number,
c is 0 or a positive number,
b/a is from 0 to 100, and
c/a is from 0 to 10,
wherein at least one of R$^1$, R$^2$, R$^3$, R$^4$, and R$^5$ is SIL$_1$-X; and
R$^6$ is selected from the group consisting of C$_1$-C$_{20}$ alkyl, C$_2$-C$_8$ alkenyl, C$_5$-C$_8$ cycloalkyl, phenyl, phenyl C$_1$-C$_3$ alkyl, trimethylphenol, and fluorine, wherein R$_3$ is SIL$_1$-X and the SIL$_1$-X is selected from the group consisting of:

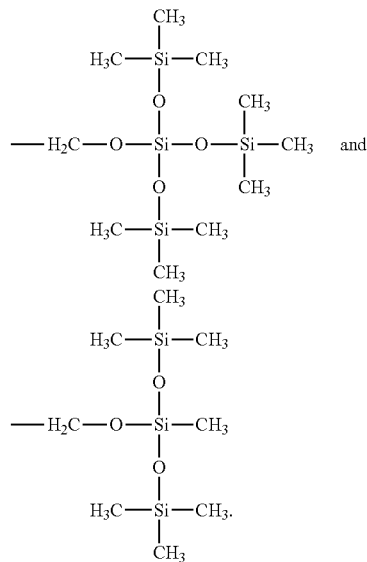
and

2. The photoinitiator according to claim 1, wherein R$^1$ and R$^5$ are methyl groups and R$^2$ and R$^4$ are hydrogen.

3. A photoinitiator of the general Formula I:

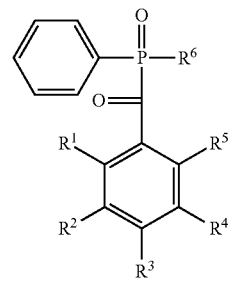

wherein:
R$^1$, R$^2$, R$^3$, R$^4$, and R$^5$ are the same or different and are selected from the group consisting of SIL$_1$-X, hydrogen, C$_1$-C$_{20}$ alkyl, C$_2$-C$_8$ alkenyl, C$_5$-C$_8$ cycloalkyl, phenyl C$_1$-C$_3$ alkyl, and fluorine;
X is optional, and if present is C$_1$-C$_{12}$ alkyl;
SIL$_1$ has the general formula:

$(R^7SiO_{3/2})_a(R^7{}_2SiO_{2/2})_b(R^7{}_3SiO_{1/2})_c$ wherein:
R$^7$ is selected from the group consisting of C$_1$-C$_{20}$ alkyl, C$_2$-C$_8$ alkenyl, C$_5$-C$_8$ cycloalkyl, alkoxyl, phenyl, and phenyl C$_1$-C$_3$ alkyl;
a is a positive number,
b is 0 or a positive number,
c is 0 or a positive number,
b/a is from 0 to 100, and
c/a is from 0 to 10,
wherein at least one of R$^1$, R$^2$, R$^3$, R$^4$, and R$^5$ is SIL$_1$-X; and
R$_6$ is selected from the group consisting of a phenyl group, CH$_3$CH$_2$O—, and a trimethylphenol group.

4. The photoinitiator according to claim 1, wherein $R_6$ is selected from the group consisting of a phenyl group, $CH_3CH_2O-$, and a trimethylphenol group.

5. The photoinitiator according to claim 2, wherein $R_6$ is selected from the group consisting of a phenyl group, $CH_3CH_2O-$, and a trimethylphenol group.

6. A compound selected from the group consisting of:

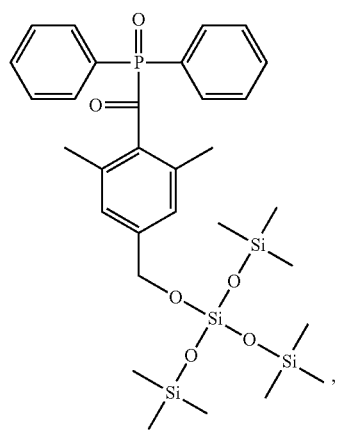

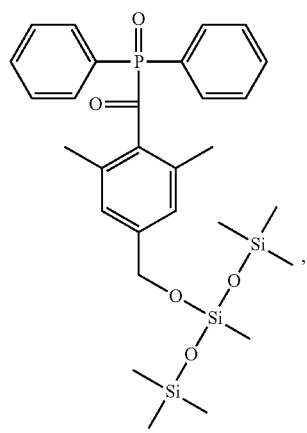

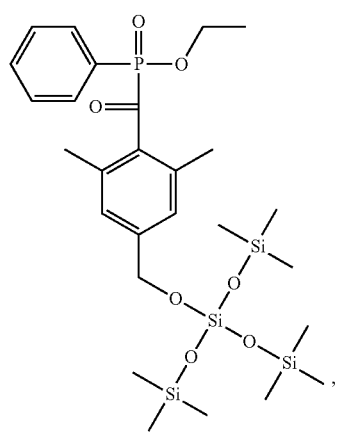

-continued

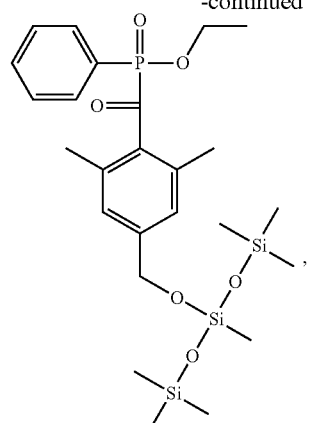

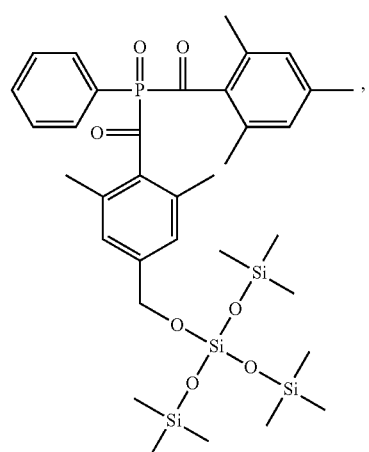

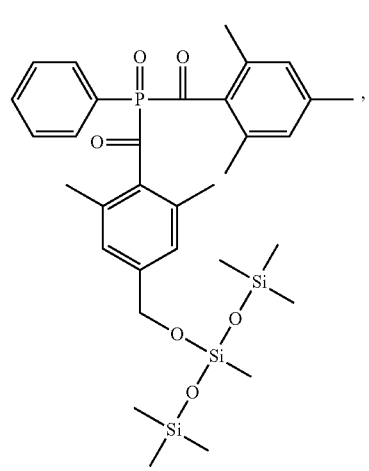

and combinations thereof.

7. A method of synthesizing a compound of the general Formula I:

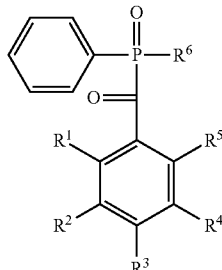

wherein:

R¹, R², R³, R⁴, and R⁵ are the same or different and are selected from the group consisting of $SIL_1$-X, hydrogen, $C_1$-$C_{20}$ alkyl, $C_2$-$C_8$ alkenyl, $C_5$-$C_8$ cycloalkyl, phenyl $C_1$-$C_3$ alkyl, and fluorine;

X is optional, and if present is $C_1$-$C_{12}$ alkyl;

$SIL_1$ has the general formula:

$$(R^7SiO_{3/2})_a(R^7{}_2SiO_{2/2})_b(R^7{}_3SiO_{1/2})_c$$

wherein:
  R⁷ is selected from the group consisting of $C_1$-$C_{20}$ alkyl, $C_2$-$C_8$ alkenyl, $C_5$-$C_8$ cycloalkyl, alkoxyl, and phenyl $C_1$-$C_3$ alkyl;
  a is a positive number,
  b is 0 or a positive number,
  c is 0 or a positive number,
  b/a is from 0 to 100, and
  c/a is from 0 to 10,
wherein at least one of R¹, R², R³, R⁴, and R⁵ is $SIL_1$-X; and R⁶ is selected from the group consisting of $C_1$-$C_{20}$ alkyl, $C_2$-$C_8$ alkenyl, $C_5$-$C_8$ cycloalkyl, phenyl, phenyl $C_1$-$C_3$ alkyl, trimethylphenol, and fluorine, comprising the steps of:

1) Activating a compound of Formula A:

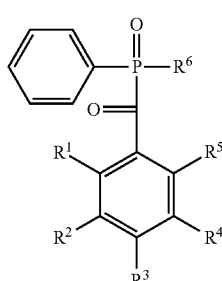

wherein R¹, R², R³, R⁴, and R⁵ are as above, but none may be $SIL_1$-X, to produce a compound of Formula B:

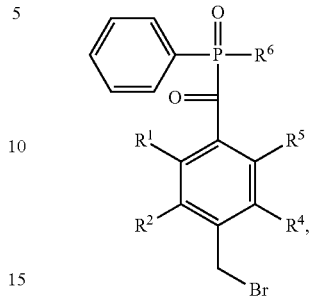

2) Subjecting the compound of Formula B to a nucleophilic acetate substitution reaction to produce a compound of Formula C:

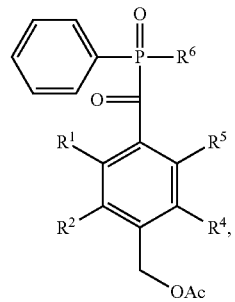

3) Subjecting the compound of Formula C to a hydrolysis reaction to produce a compound of Formula D:

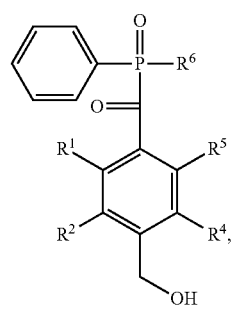

and

4) Subjecting the compound of Formula D to a condensation reaction with a compound having the formula $SIL_1$-X—Cl or $SIL_1$-X—H to produce the compound of Formula 1.

8. A composition comprising:
  a) about 70 to about 99.9 weight percent of a photocurable silicone; and
  b) about 0.1 to about 10.0 weight percent of a compound of the general Formula I:

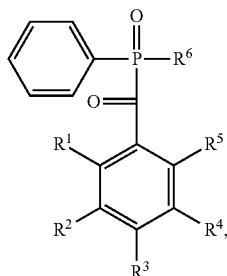

wherein:

$R^1$, $R^2$, $R^3$, $R^4$, and $R^5$ are the same or different and are selected from the group consisting of $SIL_1$-X, hydrogen, $C_1$-$C_{20}$ alkyl, $C_2$-$C_8$ alkenyl, $C_5$-$C_8$ cycloalkyl, phenyl $C_1$-$C_3$ alkyl, and fluorine;

X is optional, and if present is $C_1$-$C_{12}$ alkyl;

$SIL_1$ has the general formula:

$(R^7SiO_{3/2})_a(R^7{}_2SiO_{2/2})_b(R^7{}_3SiO_{1/2})_c$ wherein:

$R^7$ is selected from the group consisting of $C_1$-$C_{20}$ alkyl, $C_2$-$C_8$ alkenyl, $C_5$-$C_8$ cycloalkyl, alkoxyl, phenyl, and phenyl $C_1$-$C_3$ alkyl;

a is a positive number, b is 0 or a positive number, c is 0 or a positive number, b/a is from 0 to 100, and c/a is from 0 to 10, wherein at least one of $R^1$, $R^2$, $R^3$, $R^4$, and $R^5$ is $SIL_1$-X; and $R^6$ is selected from the group consisting of $C_1$-$C_{20}$ alkyl, $C_2$-$C_8$ alkenyl, $C_5$-$C_8$ cycloalkyl, phenyl, phenyl $C_1$-$C_3$ alkyl, trimethylphenol, and fluorine.

9. The composition according to claim 8, wherein $R_3$ is $SIL_1$-X and the $SIL_1$-X is selected from the group consisting of:

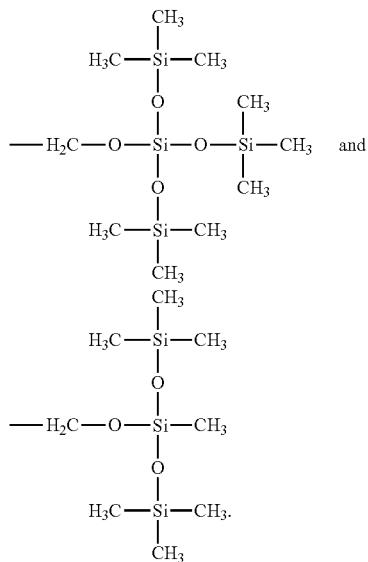

10. The composition according to claim 9, wherein $R^1$ and $R^5$ are methyl groups and $R^2$ and $R^4$ are hydrogen.

11. The composition according to claim 8, wherein $R_6$ is selected from the group consisting of a phenyl group, $CH_3CH_2O$—, and a trimethylphenol group.

12. The composition according to claim 9, wherein $R_6$ is selected from the group consisting of a phenyl group, $CH_3CH_2O$—, and a trimethylphenol group.

13. The composition according to claim 10, wherein $R_6$ is selected from the group consisting of a phenyl group, $CH_3CH_2O$—, and a trimethylphenol group.

14. The composition according to claim 8, wherein the compound of the general Formula I is selected from the group consisting of:

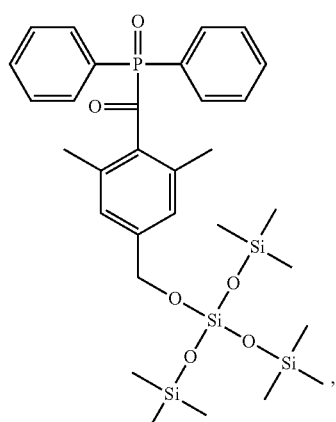

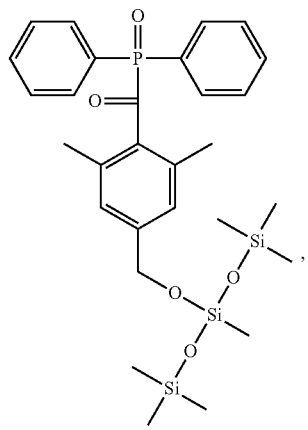

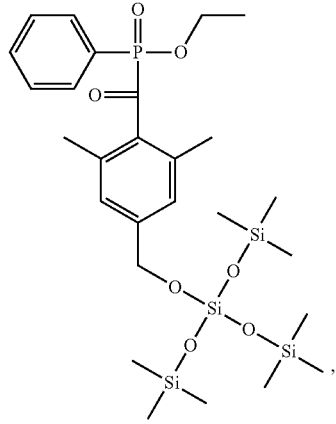

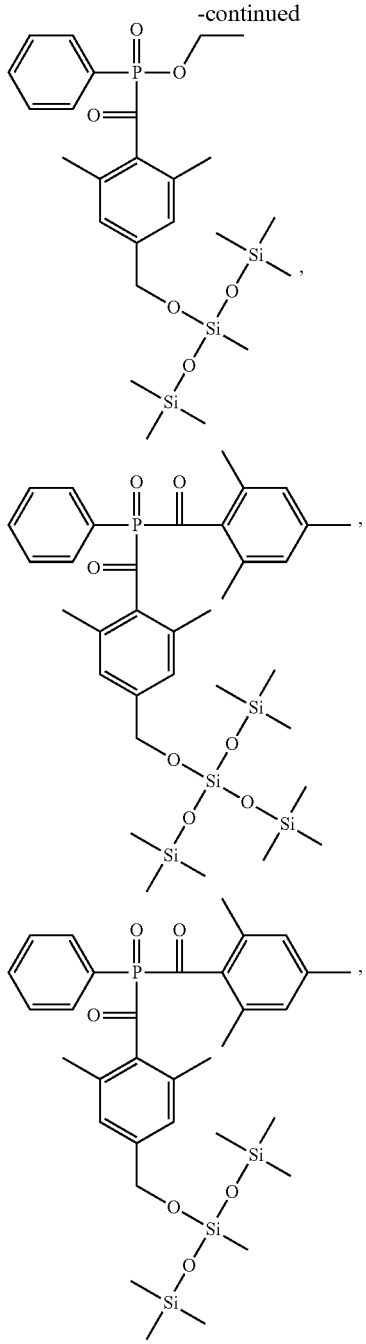

and combinations thereof.

15. The composition according to claim 8, wherein the photocurable silicone is a UV curable organosilicone or a UV and moisture dual cure silicone.

16. The composition according to claim 8, wherein the photocuable silicone is a (meth)acrylic endcapped silicone.

17. The composition according to claim 8, wherein the photocuable silicone is a (meth)acrylic endcapped silanol terminated polydimethylsiloxane.

18. A method of making a silicone polymer product, comprising the steps of:
A) Providing a photocurable silicone composition comprising:
i) about 70 to about 99.9 weight percent of a photocurable silicone; and
ii) about 0.1 to about 10.0 weight percent of a compound of the general Formula I:

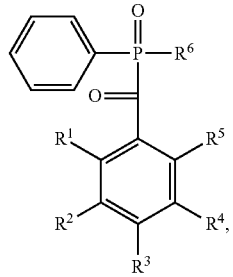

wherein:
$R^1$, $R^2$, $R^3$, $R^4$, and $R^5$ are the same or different and are selected from the group consisting of $SIL_1$-X, hydrogen, $C_1$-$C_{20}$ alkyl, $C_2$-$C_8$ alkenyl, $C_5$-$C_8$ cycloalkyl, phenyl $C_1$-$C_3$ alkyl, and fluorine;
X is optional, and if present is $C_1$-$C_{12}$ alkyl;
$SIL_1$ has the general formula:

$$(R^7SiO_{3/2})_a(R^7{}_2SiO_{2/2})_b(R^7{}_3SiO_{1/2})_c$$

wherein:
$R^7$ is selected from the group consisting of $C_1$-$C_{20}$ alkyl, $C_2$-$C_8$ alkenyl, $C_5$-$C_8$ cycloalkyl, alkoxyl, phenyl, and phenyl $C_1$-$C_3$ alkyl;
a is a positive number,
b is 0 or a positive number,
c is 0 or a positive number,
b/a is from 0 to 100, and
c/a is from 0 to 10,
wherein at least one of $R^1$, $R^2$, $R^3$, $R^4$, and $R^5$ is $SIL_1$-X; and
$R^6$ is selected from the group consisting of $C_1$-$C_{20}$ alkyl, $C_2$-$C_8$ alkenyl, $C_5$-$C_8$ cycloalkyl, phenyl, phenyl $C_1$-$C_3$ alkyl, trimethylphenol, and fluorine; and
B) Exposing the photocurable silicone composition to ultraviolet radiation or visible light to initiate photocuring of the photocurable silicone composition to produce the silicone polymer product.

19. The method according to claim 18, wherein the photocurable silicone is a UV curable organosilicone or a UV and moisture dual cure silicone.

20. The method according to claim 18, wherein the photocurable silicone is a (meth)acrylic endcapped silicone.

21. The method according to claim 18, wherein the photocurable silicone is a (meth)acrylic endcapped silanol terminated polydimethylsiloxane.

22. The method according to claim 18, wherein the ultraviolet radiation has a wavelength of about 390 nanometers or greater.

23. The method according to claim 18, wherein the ultraviolet radiation has a wavelength of about 405 nanometers.

24. The method of making a silicone polymer product of claim 18, further comprising the step of placing the photocurable silicone composition in contact with at least one layer of an optically clear composition prior to the initiation of photocuring, wherein when the photocurable silicone composition is cured the silicone polymer product is suitable for use in an optically clear display.

25. The method of making a silicone polymer product of claim 24, wherein the optically clear composition is glass.

26. The method of making a silicone polymer product of claim 24, further comprising the step of placing the photocurable silicone composition between two layers of an optically clear composition prior to the initiation of photocuring, wherein when the photocurable silicone composition is cured the silicone polymer product is suitable for use in an optically clear display.

27. The method of making a silicone polymer product of claim 26, wherein the optically clear composition is glass.

28. The method of making a silicone polymer product of claim 26, wherein the silicone polymer product has a haze value of about 1 or less and a yellowness value of about 1 or less at a gap of 750 micrometers between the two layers of the optically clear composition when aged for 500 hours in a QUV test machine or when aged for 500 hours in an oven at 85° C. and 85% relative humidity.

* * * * *

UNITED STATES PATENT AND TRADEMARK OFFICE
CERTIFICATE OF CORRECTION

PATENT NO.       : 10,597,413 B2
APPLICATION NO.  : 16/031023
DATED            : March 24, 2020
INVENTOR(S)      : Wenjuan Tan et al.

Page 1 of 1

It is certified that error appears in the above-identified patent and that said Letters Patent is hereby corrected as shown below:

Column 31, Line 58: Change "photcuable" to --photocurable--.

Column 31, Line 60: Change "photcuable" to --photocurable--.

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*